United States Patent [19]

Fife et al.

[11] Patent Number: 4,874,558

[45] Date of Patent: Oct. 17, 1989

[54] POLYMER CATALYZED SYNTHESIS OF ACID ANHYDRIDES

[75] Inventors: Wilmer K. Fife, Indianapolis, Ind.; Zhi-Dong Zhang, Tianjin, China

[73] Assignee: Indiana University Foundation, Bloomington, Ind.

[21] Appl. No.: 284,846

[22] Filed: Dec. 13, 1988

Related U.S. Application Data

[63] Continuation-in-part of Ser. No. 52,439, May 21, 1987.

[51] Int. Cl.$^4$ ............................................. C07C 51/56
[52] U.S. Cl. .................................. 562/894; 562/895; 562/897
[58] Field of Search ................................ 260/548, 546

[56] References Cited

U.S. PATENT DOCUMENTS

| | | | |
|---|---|---|---|
| 2,843,470 | 7/1958 | Searle | 260/546 |
| 3,097,238 | 7/1963 | Blatz | 260/546 |
| 4,024,129 | 5/1977 | Henniger et al. | 260/546 |

FOREIGN PATENT DOCUMENTS

| | | | |
|---|---|---|---|
| 100450 | 4/1917 | United Kingdom | 260/548 |
| 128282 | 6/1919 | United Kingdom | 260/548 |
| 313234 | 1/1929 | United Kingdom | 260/548 |

OTHER PUBLICATIONS

Vlietstra, E. J. et al., J. Neth. Chem. Soc., 101:460–461, (1982).
Stevens W. and Van Es, A., Recueil, 83:1287–1293, (1964).
Schijf, R. et al., Recueil, 84:594–596, (1965).
Scriven, E. F., Chem. Soc. Rev., 12:129–161, (1983).
Fife, W. K. and Dally, R. D., Amer. Chem. Soc. Abst., 187:251, (1984).
Fersht, A. R. and Jencks, W. P., J. Am. Chem. Soc., 92:5432–5442, (1970).
Ibid., 92:5442–5452, 1970.
Mathias, L. J. and Vaidya, R. A., J. Am. Chem. Soc., 108:1093–1094, (1986).
Hofle et al., Agnew. Chem. Int. Ed. Engl., 17:569–583, (1978).
Akelah, A. and Sherrington, D. C., Chem. Rev., 81:557–587, (1981).
Akelah, A. Synthesis, 413–438, (Jun. 1981).
Boivin, S. et al., Bull. Soc. Chim. Fr. II, (5–6):201–203, (1984).
Ralitsch, M. et al., Chem. Abstr., 97:181272m, (1982).
Shai, Y. et al., J. Am. Chem. Soc., 107:4249–4252, (1985).
Tomoi, M. et al., Makromol, Chemie, 6(6):397–401, (1985).

*Primary Examiner*—Paul J. Killos
*Attorney, Agent, or Firm*—Kirkland & Ellis

[57] ABSTRACT

Solid-phase copolymers of 4-vinylpyridine or 4-vinylpyridine 1-oxide may be employed as catalysts in the formation of acid anhydrides. A water soluble polymer of 4-vinylpyridine 1-oxide may also be employed as a catalyst in the formation of acid anhydrides.

15 Claims, No Drawings

POLYMER CATALYZED SYNTHESIS OF ACID ANHYDRIDES

This is a continuation-in-part of co-pending application Ser. No. 52,439 filed on May 21, 1987.

BACKGROUND OF THE INVENTION

A. Field of the Invention

This invention relates to the synthesis of acid anhydrides from carboxylic acids and acid halides using solid phase co-polymers as catalysts.

B. Prior Art

Acid anhydrides are among the most important classes of reagents in organic chemistry. They are frequently the preferred reactive acid derivatives for preparation of esters, amides, and peptides. Further, anhydrides of formic acid are potentially very useful formylating agents. However, among the group of anhydrides which may potentially act as formylating agents, only acetic formic anhydride has been used extensively. Symmetrical formic anhydride, the formylating agent of choice, has not often been employed because it is highly unstable and can only be handled at temperatures below −40° C. It readily decomposes to formic acid and carbon monoxide. Moreover, most mixed formic anhydrides are also unstable since they are prone to disproportionation or decomposition particularly in the presence of catalysts used in their synthesis.

In the past, anhydrides most commonly have been synthesized from acid halides (usually the chlorides) and carboxylic acids by means of transacylation reactions. These transacylation reactions utilize nucleophilic catalysts such as pyridine. Acid halides are known to acylate pyridine catalysts forming acylpyridinium intermediates and to acylate other tertiary amines to form acylammonium ions which, in turn, react with carboxylate ions to form the desired anhydride.

Although these amine catalysts are effective in forming anhydrides, their use has several disadvantages. For example, transacylation catalysts often further catalyze the disproportionation of newly formed mixed anhydride products and the decomposition of other unstable anhydride products. Stevens, W. & Van es, A. Recl. Trav. Chim. Pays-Bas. 83: 1287 (1964) and Ibid. 84: 704 (1965). Moreover, additional purification steps are required to separate these catalysts from the product and regenerate them for repeated use. See R. K. Smalley and H. Suschitzky, *J. Chem. Soc.* 755 (1964).

The simplicity and convenience of processes that use solid-phase polymeric reagent/catalysts has been generally acknowledged. See for example, A. Akelah and D. C. Sherrington, 81 *Chem. Rev.* 557 (1981); A. Akelah, *Synthesis* 413 (1981); S. Bowin et al. *Bull. Soc. Chim. Fr.* II-201 (1984); M. Ralitsch et al. 13 *Rev. Latinoam. Quim.* 16 (1982) and Y. Shai et al., 107 *J. Am. Chem. Soc.* 4249 (1985). However only a small number of applications of this methodology to transacylation reactions have been reported. No application of a polymeric catalyst/reagent to anhydride synthesis has ever been reported.

Accordingly, it is an object of the present invention to provide a method of synthesis of anhydrides using solid-phase polymeric catalysts and soluble polymeric catalysts in single and mixed solvent systems.

It is another object of the present invention to provide solid phase and soluble polymeric catalysts which do not degrade or disproportionate the anhydride products.

It is a further object of the present invention to provide a method for synthesizing stable anhydrides of formic acid.

SUMMARY OF THE INVENTION

The foregoing objects, advantages and features of the present invention may be achieved with a process for preparing acid anhydrides comprising the step of reacting a carboxylic acid or carboxylate salt with an acid halide or an acyl activating agent in the presence of a solid phase copolymer of 4-vinylpyridine, a solid phase copolymer of 4-vinylpyridine 1-oxide, and a water soluble homopolymer of 4 vinylpyridine 1-oxide, as a catalyst. More particularly, the present invention involves a process for preparing a process for preparing acid anhydrides comprising the step of reacting an acid halide with a carboxylic acid or carboxylate salt in the presence of a catalyst selected from a group consisting of a solid phase co-polymer of 4-vinylpyridine and a solid phase co-polymer of 4-vinylpyridine 1-oxide. Alternatively, symmetrical anhydrides may be prepared by reacting a carboxylic acid or carboxylate salt with an acyl activating agent in the presence of a solid-phase copolymer of 4-vinylpyridine. In another alternative embodiment, acid anhydrides may be prepared by reacting an acid halide and carboxylic acid or carboxylate salt in the presence of a water soluble polymer of 4-vinylpyridine 1-oxide as a catalyst.

DETAILED DESCRIPTION OF THE INVENTION

A. Solid Phase Polymeric Catalyst with Pendant Pyridine Groups: 4-Vinylpyridine Copolymer Catalyst Mixed and symmetrical anhydrides of the structural formula:

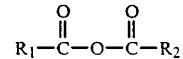

can be prepared by the process of the present invention by reacting an acid halide with a carboxylic acid or a carboxylate salt in the presence of a solid-phase copolymer 4-vinylpyridine ("P4-VP"). Approximately 3 to 10 equivalents of such polymer (based on pyridine) and preferably 3 to 5 equivalents, per mole of carboxylic acid, can be used. In addition, approximately 0.1 equivalents of such polymer (based on pyridine) per mole of carboxylate salt can be used. The acid halide used in the process of the invention has the structural formula:

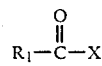

wherein $R_1$ is any saturated or unsaturated alkyl or aralkyl, substituted or unsubstituted aryl or alkaryl and alkoxy or aralkoxy, e.g., methyl, ethyl, isopropyl, tert-butyl, n-pentyl, n-undecyl, vinyl, isopropenyl, benzyl, styryl, phenyl, biphenylyl, 4-chlorophenyl, 4-nitrophenyl, 3,5-dinitrophenyl, 4-methoxyphenyl, 2-tolyl, 4-tolyl, p-(n-hexyl)phenyl, ethoxy, isobutoxy, and benzyloxy and wherein X is a halogen such as fluorine, chlorine, and bromine.

The carboxylic acid used in the process of this invention has the structural formula:

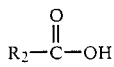

wherein $R_2$ is any saturated or unsaturated alkyl or aralkyl and substituted or unsubstituted aryl or alkaryl, e.g., hydrogen, methyl, ethyl, isopropyl, tert-butyl, n-pentyl, n-undecyl, vinyl, isopropenyl, benzyl, styryl, phenyl, 4-chlorophenyl, 4-nitrophenyl, 3,5-dinitrophenyl, 4-methoxyphenyl, 2-tolyl, and 4-tolyl.

The carboxylate salt used in the process of this invention has the structural formula:

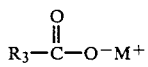

wherein $R_3$ is the same as $R_2$ above and $M^+$ is a monovalent cation, such as lithium, sodium, potassium, cesium and tetraalkylammonium.

P4-VP may also be used as a catalyst in the formation of symmetrical anhydrides from a mixture of one of the above described carboxylic acids or carboxylate salts and approximately 0.55 equivalents of an acyl activating agent such as thionyl chloride, phosgene, phosphorus halides (such as $(PO)_2POCl$, $R_2POCl$, $POCl_3$, $PCl_3$, $PBr_3$, $PCl_5$, $PBr_5$) and other sulfur chlorides (such as $PhSO_2Cl$, $SO_2Cl_2$).

P4-VP is made by copolymerizing and crosslinking 4-vinylpyridine with 1-25% 4:1 divinylbenzene-4-ethylstyrene. P4-VP contains 0.007 equivalents pyridine per gram and is available under the trade name Reillex 425 from Reilly Tar and Chemical Corporation, Indianapolis, Ind.

In the preferred embodiment P4-VP is used to catalyze the reaction of an acid halide with a carboxylic acid to form an anhydride. An appropriate organic reagent such as, dichloromethane is employed as the solvent. Other non-nucleophilic solvents such as tetrahydrofuran, acetonitrile, dimethyl sulfoxide and dimethyl formamide may be used.

The reaction can be carried out by placing the reactants, P4-VP and the solvent in a conventional round bottom flask and constantly stirring the reaction mixture at temperatures ranging from 0 degrees C. to ambient (i.e., "the batch method"). Alternatively, the P4-VP can be loosely packed in a column and the reaction effected by passing a solution of the acid halide and carboxylic acid over the solid-phase catalyst. The column is then washed with an organic solvent such as dichloromethane and the eluant subject to concentration and drying to obtain product. Hydrogen halide produced during the reaction remains bound to the P4-VP after work up; however, catalyst regeneration is easily accomplished by treatment with aqueous sodium hydroxide or carbonate, or triethylamine in dichloromethane.

EXAMPLE I

Reaction mixtures containing 0.005 moles of acid chloride, 0.006 moles of carboxylic acid, 3.0 equivalents of P4-VP (based on pyridine), and 10 ml of dichloromethane were placed in a round bottom flask and stirred for 5 to 360 minutes at temperatures of 0 degrees C. to ambient (i.e., 22 to 25 degrees C.). The organic phase was then separated from the solid-phase P4-VP by filtration. The organic phase was washed with 10% aqueous potassium carbonate, dried over anhydrous potassium carbonate and rotary evaporated to obtain the product. Table I below, sets out the acid chlorides and carboxylic acids which were used as reactants in the above-described method, the specific temperatures at which each reaction took place, the time period each reaction was stirred, and the corresponding anhydrides product which were obtained.

TABLE I
Synthesis of Anhydrides

| Reactants | | Reaction | | Anhydrides[a] | | |
|---|---|---|---|---|---|---|
| R-C(O)Cl | R-C(O)OH | Temp. °C. Time, Min. | Yield % | R-C(O)-O-C(O)-R' Composition,[b] | R'-C(O)-O-C(O)-R' Mole % | R-C(O)-O-C(O)-R Mole % |
| Mixed Anhydrides | | | | | | |
| R = Ph | R' = CH₃ | rt/5 | 64.8[c] | 0.82[d] | 0.09 | 0.09 |
| Ph | CH₃ | rt/5 | 80.0 | 0.73[d] | 0.12 | 0.15 |
| Ph | CH₃ | 0/60 | 86.4 | 0.74[d] | 0.12 | 0.14 |
| CH₃ | Ph | 0/15 | 84.9 | 0.75[d] | 0.09 | 0.16 |
| Ph | (CH₃)₂CH | 0/10 | 97.8 | 0.80 | 0.04 | 0.16 |
| Ph | (CH₃)₃C | 0/10 | 82.6 | 0.69 | 0.12 | 0.19 |
| Ph | CH₃(CH₂)₄ | 0/10 | 91.5 | 0.76[d] | 0.16 | 0.08 |
| CH₃(CH₂)₄ | Ph | 0/10 | 94.6 | 1.00[d] | 0 | 0 |
| Ph | CH₃(CH₂)₁₀ | 0/210 | 91.6 | 0.41[d,e] | 0.39 | 0.20 |
| CH₃(CH₂)₁₀ | Ph | 0/60 | 90.6 | 1.00[d,e] | 0 | 0 |
| Ph | CH₂=CH | 0/90 | 84.5 | 0.96[d,e] | 0 | 0.04 |
| Ph | CH₂=C(CH₃) | 0/60 | 97.7 | 0.90[d,e] | 0.02 | 0.08 |
| CH₃CH₂O | Ph | 0/30 | 80.3 | 1.00 | 0 | 0 |
| (CH₃)₂CHCH₂O | Ph | rt/30 | 90.4 | 0.97 | 0.03 | 0 |
| PhCH₂O | Ph | 0/30 | 75.5 | 1.00 | 0 | 0 |
| Ph | 2-CH₃Ph | rt/240 | 90.5 | 1.00[d] | 0 | 0 |
| Ph | 4-CH₃Ph | rt/180 | 91.3 | 1.00[d] | 0 | 0 |
| 2—CH₃Ph | 4-CH₃Ph | rt/240 | 89.8 | 1.00[d] | 0 | 0 |
| 4—CH₃OPh | Ph | rt/60 | 95.2 | 1.00[d] | 0 | 0 |
| Ph | 4-NO₂Ph | rt/120 | 97.6 | 0.95[d] | 0 | 0.05 |
| Ph | 3,5-(NO₂)₂Ph | rt/60 | 95.6 | 0.92 | 0 | 0.08 |
| PhSO₂Cl | CH₂=C(CH₃) | rt/60 | 68.0 | 1.00 | 0 | 0 |
| Symmetric Anhydrides | | | | | | |
| R = CH₃(CH₂)₁₀ | CH₃(CH₂)₁₀ | rt/60 | 87.2 | 1.00 | — | — |
| 2-CH₃Ph | 2-CH₃Ph | rt/360 | 90.8[d] | 1.00 | — | — |

TABLE I-continued

| Reactants | | Reaction | | Anhydrides[a] | | |
|---|---|---|---|---|---|---|
| $R\overset{O}{\underset{\|}{-}}Cl$ | $R\overset{O}{\underset{\|}{-}}OH$ | Temp. °C. Time, Min. | Yield % | Composition,[b] $R-\overset{O}{\underset{\|}{C}}-O-\overset{O}{\underset{\|}{C}}-R'$ | Mole % $R'-\overset{O}{\underset{\|}{C}}-O-\overset{O}{\underset{\|}{C}}-R'$ | $R-\overset{O}{\underset{\|}{C}}-O-\overset{O}{\underset{\|}{C}}-R$ |
| 4-CH₃Ph | 4-CH₃Ph | rt/180 | 93.2[c] | 1.00 | — | — |

[a]Product identity was established by comparison of melting point, ¹H—NMR, and/or IR data with published values except where noted otherwise.
[b]Product composition was estimated by integration of NMR spectra.
[c]Reaction catalyzed by 1.6 equivalents P4-VP was incomplete. Product mixture contained 23.3% unreacted benzoyl chloride based on starting reactant.
[d]Mass spectral analysis showed the appropriate molecular ion.
[e]No published data are available for this compound.

The data in Table I demonstrates the advantages of the method of the present invention. As previously noted, when mixed anhydrides are formed in the presence of traditional transacylation catalysts, disporportionation and degradation occur, resulting in low yields of the desired anhydride. As can be seen from Table I, high yields of the desired mixed and symmetrical anhydrides are easily obtained using this method. For example, P4-VP catalyzes the reaction of alkoyl chloride and arylcarboxylic acid to form alkylcarboxylic arylcarboxylic anhydride in high yields and without disporportionation.

An alternative preferred embodiment of the above-described method employs P4-VP as a catalyst in the synthesis of symmetrical anhydrides. Symmetrical anhydrides are important in many transacylation reactions because the formation of side products due to attack at the second acyl carbonyl of mixed anhydrides is avoided. This is especially true in derivatization reactions of relatively weak acids, because their carbonyl groups are relatively unreactive to nucleophiles. It is also important in solid-phase peptide synthesis where acylation product of high purity is essential.

In this alternative preferred embodiment symmetrical anhydrides may be synthesized by reacting a carboxylic acid or carboxylate salt with an acyl activating agent in the presence of P4-VP and in an appropriate organic solvent such as dichloromethane. The acyl activating agent employed in this invention can be thionyl chloride, phosgene, phosphorus halides (such as (RO)₂POCl, R₂POC2, POCl₃, PCl₃, PBr₃, PCl₅, PBr₅) or other sulfur chlorides (such as PhSO₂Cl, SO₂Cl₂). The carboxylic acid used in this alternative embodiment has the structural formula:

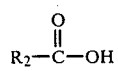

wherein R₂ is any saturated or unsaturated alkyl or aralkyl and substituted or unsubtituted aryl or alkaryl, e.g., hydrogen, methyl, ethyl, isopropyl, tert-butyl, vinyl, isopropenyl, benzyl, styryl, phenyl, 4-chlorophenyl, 4-nitrophenyl, 3,5-dinitrophenyl, 4-methoxyphenyl, 2-tolyl, 4-tolyl and p-(n-hexyl)phenyl.

The carboxylate salt of the present invention has the structural formula:

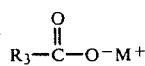

wherein R₃ is the same as R₂ above and and M⁺ is a monovalent cation such as lithium, sodium, potassium, cesium, silver or tetraalkylammonium.

This reaction may be carried out as previously described above, in the batch method with stirring or by loosely packing a column with P4-VP and then passing a mixture of carboxylic acid or carboxylate salt and acyl activating agent through the column. The column is then washed with organic solvent and the eluant collected and concentrated.

Using this alternative method, the carboxylic acid is converted directly to its related anhydride by treatment with the acyl activates agent through the catalytic action of P4-VP. During the reaction P4-VP binds gaseous, acidic side products, but is easily regenerated by treatment with excess triethylamine in dichloromethane or aqueous hydroxide or carbonate for repeated use.

EXAMPLE II

Mixtures containing about 0.005 mole carboxylic acid, 3.5–4.0 equivalents of P4-VP (based on pyridine) and 20 ml dichloromethane were treated with 0.55 equivalents thionyl chloride in 20 ml dichloromethane, either in one portion or dropwise, and stirred for 5 to 120 minutes at 22–25 degrees C. (ambient). P4-VP was removed by filtration and the remaining organic solution was rotary evaporated yielding pure samples of anhydrides. Product identity was established by comparison of melting point, ¹H-NMR and/or IR data with published values. Table II below, describes the carboxylic acids which were used as reactants in the above-described method, the method of thionyl chloride addition used in each synthesis and the yield of the corresponding anhydride product.

TABLE II

Synthesis of Symmetrical Anhydrides, batch mode

| Reactant, RCOOH | Thiomyl Chloride Addition | Conditions Time (Min) | Anhydride Yield (%) |
|---|---|---|---|
| CH₃COOH | One portion | 5 | 88.8 |
| CH₃CH₂COOH | One portion | 5 | 96.0 |
| (CH₃)₂CHCOOH | One portion | 5 | 94.6 |
| CH₂=CHCOOH | Dropwise, 20 min | 120 | 55.6[a,b] |
| CH₂=CHCOOH | Dropwise, 20 min | 60 | 52.5[b] |
| CH₂=C(CH₃)COOH | Dropwise, 20 min | 60 | 86.5 |
| PhCH=CHCOOH | Dropwise, 20 min | 60 | 89.7 |
| PhCOOH | Dropwise, 20 min | 60 | Trace[c] |
| PhCOOH | Dropwise, 20 min | 60 | 98.6 |
| 4-CH₃PhCOOH | Dropwise, 20 min | 60 | 100 |
| 4-CH₃OPhCOOH | Dropwise, 20 min | 60 | 100 |
| 4-ClPhCOOH | Dropwise, 20 min | 60 | 96.9 |
| CBZ-Alanine[e] | Dropwise, 20 min | 60 | 81.6 |

TABLE II-continued

Synthesis of Symmetrical Anhydrides, batch mode

| Reactant, RCOOH | Thionyl Chloride Addition | Conditions Time (Min) | Anhydride Yield (%) |
|---|---|---|---|
| BOC-Phenylalanine[f] | Dropwise, 20 min | 60 | [d] |

[a]Reaction temperature - 0° C.
[b]An excellent material balance for the reaction is obtained with the mass discrepancy for product just equal to mass gain by P4-VP.
[c]Control experiment in which no P4-VP was used.
[d]Product mixture contained acids and anhydrides with and without the BOC group.
[e]CBZ-Alanine is N—t-Butoxycarbonyl-L-alanine.
[f]BOC-Phenylalanine is N—t-Butoxycarbonyl-L-phenylalanine.

EXAMPLE III

A column was loosely packed with P4-VP (9–10 equivalents based on pyridine) and a solution of 0.005 mole carboxylic acid, 0.55 equivalent thionyl chloride, and 20 ml dichloromethane was passed through it. The flow rate was adjusted to provide contact/reaction time of either 10 or 20 minutes. The column was washed with dichloromethane to remove the product, and the dichloromethane solution was subjected to rotatory evaporation. The anhydride products were obtained in a high state of purity after evaporation. Product identity was established by comparison of melting point, $^1$H-NMR and/or IR data with published values. Table III below, sets forth the reactants used and the percent yields of anhydride obtained employing the above described method.

TABLE III

Synthesis of Symmetrical Anhydrides, column mode

| Reactant, RCOOH | Contact Time (Min.) | Anhydride Yield (%) |
|---|---|---|
| CH$_3$CHOOH | 10 | 88.6 |
| CH$_3$CH$_2$COOH | 10 | 95.0 |
| (CH$_3$)$_2$CHCOOH | 10 | 94.5 |
| (CH$_3$)$_3$CCOOH | 10 | 96.6 |
| PhCOOH | 20 | 98.3 |
| 4-CH$_3$PhCOOH | 20 | 98.8 |

As the data in Tables II and III demonstrate, when the method of the present invention is utilized, yields of anhydride are generally high.

Tables II and III also demonstrate that the conversion of CBZ-alanine to its anhydride derivative is a useful procedure. However, more easily deblocked amino acids such as BOC-phenylalanine are decomposed during anhydride formation. Acrylic acid gives poor yields due to polymerization, presumably of the anhydride during reaction. The more stable unsaturated acids, methacrylic acid and cinnamic acid, give high yields of the related anhydride.

The methods of these alternative embodiments of the present invention then, represent an extremely convenient procedure for obtaining a wide variety of symmetrical acid anhydrides in high yield, generally greater than ninety percent, and in a sufficiently pure state for direct use in subsequent reactions.

B. Solid-Phase Polymeric Catalysts with Pendant Pyridine-1-Oxide Groups: 4-Vinylpyridine 1-Oxide Copolymer Catalyst Mixed and symmetrical anhydrides may also be prepared by reacting an acid halide with a carboxylic acid or carboxylate salt in the presence of a solid-phase copolymer of 4-vinylpyridine 1-oxide ("P4-VP-NO") approximately 3 to 10 equivalents of such polymer (based on pyridine-1-oxide) and preferably 3 to 5 equivalents, per mole of carboxylic acid can be used. In addition, approximately 0.1 equivalents of such polymer (based on pyridine-1-oxide) per mole carboxylate salt can be used. The acid halide of this invention has the structural formula:

$$R_1-\overset{O}{\underset{\|}{C}}-X$$

wherein $R_1$ is any saturated or unsaturated alkyl or aralkyl, substituted or unsubstituted aryl or alkaryl and alkoxy or aralkoxy, e.g., methyl, ethyl, isopropyl, tert-butyl, n-pentyl, n-undecyl, vinyl, isopropenyl, benzyl, styryl, phenyl, biphenylyl, 4-chlorophenyl, 4-nitrophenyl, 3,5-dinitrophenyl, 4-methoxyphenyl, 2-tolyl, 4-tolyl, p-(n-hexyl)phenyl, ethoxy, isobutoxy, and benzyloxy and wherein X is a halogen such as fluorine, chlorine, and bromine.

The carboxylic acid of this invention has the structural formula:

$$R_2-\overset{O}{\underset{\|}{C}}-OH$$

wherein $R_2$ is any saturated or unsaturated alkyl or aralkyl and substituted or unsubstituted aryl or alkaryl, e.g., hydrogen, methyl, ethyl, isopropyl, tert-butyl, n-pentyl, n-undecyl, vinyl, isopropenyl, benzyl, styryl, phenyl, biphenyl, 4-chlorophenyl, 4-nitrophenyl, 3,5-dinitrophenyl, 4-methoxyphenyl, 2-tolyl, 4-tolyl, and p-(n-hexyl)phenyl.

The carboxylate salt of this invention has the structural formula:

$$R_3-\overset{O}{\underset{\|}{C}}-O^-M^+$$

wherein $R_3$ is the same as $R_2$ above and $M^+$ is a monovalent cation such as lithium, sodium, potassium, cesium, silver or tetraalkylammonium.

P4-VP-NO is prepared by exposing P4-VP to 30% hydrogen peroxide in glacial acetic acid using the oxidation technique described in "Aromatic Amine Oxides" by E. Ochiai at page 24, Elsevier Publishing Company: Amsterdam, 1974. (P4-VP-NO contains 0.006 equivalents pyridine N-oxide per gram).

In the preferred embodiment, acid halide is mixed in a round bottom flask with carboxylic acid salt in the presence of P4-VP-NO and in an appropriate organic solvent, such as acetonitrile or dichloromethane. Alternatively P4-VP-NO may be packed in a column and a solution of acid halide passed through the column followed by a solution of carboxylic acid or carboxylate salt in the appropriate organic solvent.

EXAMPLE IV

Approximately equimolar quantities of an acid chloride and an alkali metal salt of the same or a different acid were placed in a round bottom flask and stirred with a catalytic amount of P4-VP-NO (0.2 g catalyst to 0.01 mole reactant) in anhydrous acetonitrile (20 ml) at ambient temperature for 50 to 90 minutes. The solid polymer was separated by filtration and the organic solution diluted with dichloromethane (50 ml), washed with 5% aqueous sodium bicarbonate (20 ml), dried over anhydrous magnesium sulfate and concentrated by rotary evaporation. The anhydride products remained as residues and were obtained in a yield of 90% or better except when thermally unstable. The identity of the products was established by IR and NMR spectral data as well as mass spectral analysis in some cases. Table IV below, describes the reactants that may be employed in using this method and the corresponding anhydrides synthesized together with their percent yield.

wherein $R_1$ is any saturated or unsaturated alkyl or aralkyl, substituted or unsubstituted aryl or alkaryl and alkoxy or aralkoxy, e.g., hydrogen, methyl, ethyl, isopropyl, tert-butyl, vinyl, isopropenyl, benzyl, styryl, phenyl, biphenylyl, 4-chlorophenyl, 4-nitrophenyl, 3,5-dinotrophenyl, 4-methoxyphenyl, 2-tolyl, 4-tolyl, p-(n-hexyl)phenyl, ethoxy, isobutoxy, and benzyloxy and wherein X is a halogen such as fluorine, chlorine, and bromine. The cinnamic formic anhydride and formic 4-methoxy benzoic anhydride produced by this method

TABLE IV
Synthesis of Anhydrides

| Reactants | | | Anhydrides | |
| --- | --- | --- | --- | --- |
| R—COCl | $R^1$—COO$^-$Na$^+$ | Yield (%) | R—CO—O—CO—R' | R'—CO—O—CO—R' |
| Mixed Formic Anhydrides | | | | |
| CH$_3$COCl | HCOO$^-$Na$^+$ | 7.2 | 0.00 | 1.00 |
| (CH$_3$)$_3$CCOCl | HCOO$^-$Na$^+$ | 47.9 | 0.83 | 0.17 |
| CH$_2$=C(CH$_3$)COCl | HCOO$^-$Na$^+$ | 10 | a | a |
| PhCH=CHCOCl | HCCO$^-$Na$^+$ | 88.7$^{d,e}$ | 0.94 | 0.06 |
| PhCOCl | HCOO$^-$Na$^+$ | 60.4 | 0.85 | 0.15 |
| p-CH$_3$PhCOCl | HCOO$^-$Na$^+$ | 77.4$^{b,c}$ | 0.88 | 0.12 |
| P—n-C$_6$N$_{13}$PhCOCl | HCOO$^-$Na$^+$ | 93.3$^{b,c}$ | 0.94 | 0.06 |
| p-CH$_3$OPhCOCl | HCOO$^-$Na$^+$ | 88.9$^{b,c}$ | 0.97 | 0.03 |
| p-PhPhCOCl | HCOO$^-$Na$^+$ | 99.8$^c$ | 0.60 | 0.40 |
| Other Mixed Anhydrides | | | | |
| PhCOCl | CH$_3$COO$^-$Na$^+$ | 100.0 | 0.78 | 0.16 |
| PhCOCl | CBZ—Ala (K$^+$ Salt) | 96.1 | 0.59 | 0.25 |
| BuOCOCl | CBZ—Ala (K$^+$ Salt) | d | — | — |
| p-CH$_3$PhCOCl | PhCOO$^-$Na$^+$ | 98.0 | 1.00 | 0.00 |
| | | | | 0.06 |
| | | | | 0.16 |
| | | | | — |
| | | | | 0.00 |

$^a$A complex product mixture included the acids as well as mixed and symmetrical anhydrides.
$^b$Mass spectral analysis showed the appropriate molecular ion.
$^c$No published data is available for this compound.
$^d$A complex product mixture included symmetrical and mixed anhydrides and the isobutyl ester of CBZ-alanine.

Mixed formic anhydrides such as cinnamic formic anhydride and formic 4-methoxybenzoic anhydride produced by this method are thermally stable at ambient temperatures. The advantage of using P4-VP-NO over known transacylation catalysts is that the pyridine-1-oxide moities can function effectively as transacylation catalysts while not promoting disproportionation or degradation of the mixed formic anhydride products. Further, the P4-VP-NO is easily isolated from the reaction mixture so that it may be used repeatedly as a catalyst.

In an additional alternative embodiment of the present invention, P4-VP-NO or P4-VP may be used to catalyze the synthesis of cinnamic formic anhydride, formic 4-methoxybenzoic anhydride and other mixed formic anhydrides from sodium formate and the appropriate acid chloride using anhydrous acetonitrile as the solvent.

The acid chloride of this alternative embodiment has the structural formula:

of the invention exhibit excellent selectivity as formylating agents of alcohols and amines.

EXAMPLE V

Reaction mixtures containing 0.0005 mole acid chloride, 1.0 equivalent dried and powdered sodium formate, 0.20 g P4-VP-NO or P4-VP and 20 ml anhydrous acetonitrile were stirred vigorously with teflon-coated stir bars for 1.5 hours at room temperature (unless otherwise noted in Table V below). Products were isolated after filtering reaction mixtures, diluting (2.5×) filtrates with dichloromethane, washing with 5% aqueous sodium bicarbonate, drying over anhydrous magnesium sulfate, and rotary evaporation. The identity of known products was established by comparison of IR and $^1$H-NMR spectral data with published values. New anhydrides gave mass spectra with appropriate molecular ions. Composition of product mixtures was estimated by integration of $^1$H-NMR spectra of isolated materials. Table V below, describes the reactants used in the above method and anhydride products obtained.

TABLE V
SYNTHESIS OF MIXED FORMIC ANHYDRIDES

| Reactants $R\overset{O}{\underset{\|}{C}}Cl$ | Total Yield (%) | Anhydrides Mole Ratio $R\overset{O}{\underset{\|}{C}}O\overset{O}{\underset{\|}{C}}N$ | $R\overset{O}{\underset{\|}{C}}O\overset{O}{\underset{\|}{C}}R$ |
|---|---|---|---|
| Catalysis By P4—VP—NO | | | |
| R = Me | 7.2 | 0.00 | 1.00 |
| Me$_3$C | 47.9 | 0.83 | 0.17 |
| Ph | 60.4 | 0.85 | 0.15 |
| 4-MeOPh | 88.9 | 0.97 | 0.03 |
| PhCH=CH | 88.7 | 0.94 | 0.06 |
| PhCH=CH[a] | 54.9 | 0.87 | 0.13 |
| PhCH=CH[b] | 71.6 | 0.96 | 0.04 |
| Catalysis By P4—VP | | | |
| PhCH=CH | 67.5 | 0.80 | 0.20 |
| PhCH=CH[a] | 56.3 | 0.92 | 0.08 |
| No Catalyst | | | |
| PhCH=CH[b] | 44.1 | 1.00 | 0.00 |

[a] Reaction mixture contained 0.005 mole acid chloride, 1.1 equivalents formic acid, 1.5 equivalents P4—VP—NO or P4—VP and 20 ml dichloromethane and it was stirred for 1 hour at 0° C. The product mixture obtained with P4—VP—NO catalysis included 12.4% unreacted cinnamoyl chloride (based on starting reactant) with P4—VP catalysis the reaction was complete.

[b] The reactions were run at 0° C. for 60 minutes. The product mixture of the uncatalyzed reaction contained 52.1% unreacted cinnamoyl chloride and 1.9% cinnamic acid. The product mixture with catalysis by P4—VP—NO contained 20.7% cinnamoyl chloride and 4.7% cinnamic acid. (based on starting reactant)

As the data in Table V demonstrates, product formation is accelerated approximately two fold by 0.10 equivalent P4-VP-NO at 0 degrees C. P4-VP, however, was not found to be an effective catalyst. Catalysis by P4-VP-NO and P4-VP gave cinnamic formic anhydride in 85% and 56% yield, respectively. These newly synthesized anhydrides are thermally stable solids.

As stated previusly, anhydrides of formic acids are used as formylating agents in numerous reactions. The utility of the formic anhydrides synthesized by the method of the present invention is demonstrated by Example VI below.

EXAMPLE VI

Four different methods can be employed when using formic anhydrides synthesized by the above-described methods, as formylating agents. In Method "A", mixtures containing equimolar quantities (0.005 mole) of mixed formic anhydride and amine or alcohol (collectively "reactants") were dissolved in 3-20 ml dichloromethane and stirred for 30 to 240 minutes. In Method "B", mixtures of 0.005 mole reactants in 20 ml dichloromethane were vigorously stirred with 1.0 equivalents potassium carbonate in 10 ml water for 30 minutes. In Method "C", mixtures of 0.005 mole reactants and 1.0 equivalents powered, anhydrous sodium bicarbonate in 2 ml anhydrous acetonitrile were stirred for 2 hours. In Method "D", mixtures of 0.005 mole reactants and 0.01 equivalents of 2,6-lutidine in 5 ml dichloromethane were stirred for 3 to 15 hours. The product identity was established by comparison of melting point, $^1$H-NMR, and/or IR data with published values. Table VI presents the data for these reactions.

TABLE VII
FORMYLATION EXPERIMENTS - REACTION CONDITIONS

| $R\overset{O}{\underset{\|}{C}}O\overset{O}{\underset{\|}{C}}N$ | Nucleophile | Method | Base/ Catalyst | Reaction Time (Min) | Formamide/ Formate Ester Yield (%) |
|---|---|---|---|---|---|
| R — PhCH=CH | PhNH$_2$ | A | — | 60 | 96.0 |
| | PhCH$_2$NHMe | A | — | 30 | 98.8 |
| | H$_2$NCH(CH$_2$Ph)CCOOMe—HCl | B | Aq K$_2$CO$_3$ | 30 | 96.3 |
| 4-MeOPh | PhNH$_2$ | A | — | 30 | 96.7 |
| | PhCH$_2$NHMe | A | — | 30 | 99.7 |
| | PhNH$_2$ | A | — | 60 | 99.0 |
| | PhNHMe | A | — | 60 | 91.2 |
| | H$_2$NCH(CH$_2$Ph)COOMe—HCl | B | Aq K$_2$CO$_3$ | 30 | 96.5 |
| | PhCH$_2$OH | A | — | 120 | 87.5 |
| | | C | NaHCO$_3$ | 120 | 78.0 |
| | Cyclohexanol | A | — | 180 | 80.7 |
| | | D | 2,6-Lutidine | 180 | 80.7 |
| | 1-Methylcyclohexanol | A | — | 240 | 81.8[a] |
| | | D | 2,6-Lutidine | 900 | 78.7[a] |

[a] bp 40° C./1.5 torr; IR (Neat) ν CO 1720 cm$^{-1}$; $^1$H—NMR (CDCl$_3$) δ 8.13, s, 1H (COH), 1.3-2.4, m, 13H (C$_6$H$_{10}$Me); MS m/z 142 (M), 96 (Base).

As shown in Table VI formic anhydrides synthesized using the method of this invention are effective in treating alcohols and amines, leading exclusively to the formylated product is essentially quantitative yield in reactions with primary and secondary amines. Product yields are also high with the less nucleophilic alcohols. Significantly, the tertiary alcohol, 1-methycyclohexanol, is readily formylated by these mixed formic anhydrides.

C. Soluble Polymeric Catalysts with Pendant 4-Vinylpyridine 1-Oxide Groups: Soluble Polymers of 4-Vinylpyridine 1-Oxide A water soluble homopolymer of 4-vinylpyridine 1-oxide ("H-P4-VP-NO") also may be employed as catalyst in the formation of symmetrical and mixed anhydrides. In this method of the present invention, a mixture of acid halide and carboxylic acid or carboxylate salt is rapidly stirred in a mixture of water and immiscible, non-nucleophilic organic solvent (e.g., acetonitrile, dichloromethane, ethylacetate, tetrahydrofuran, toluene) in the presence of H-P4-VP-NO. The acid chloride of the present invention has the structural formula:

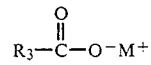

wherein $R_1$ is any saturated or unsaturated alkyl or aralkyl, substituted or unsubstituted aryl or alkaryl and alkoxy or aralkoxy, e.g., methyl, isopropyl, tert-butyl, vinyl, isopropenyl, benzyl, styryl, phenyl, 4-chlorophenyl, 4-nitrophenyl, 3,5-dinotrophenyl, 4-methoxyphenyl, 2-tolyl, 4-tolyl, ethoxy, and benzyloxy and wherein X is a halogen such as fluorine, chlorine, and bromine.

The carboxylic acid of the present invention has the structural formula:

wherein $R_2$ is any saturated or unsaturated alkyl or aralkyl and substituted or unsubstituted aryl or alkaryl, e.g., hydrogen, methyl, ethyl, isopropyl, tert-butyl, vinyl, isopropenyl, benzyl, styryl, phenyl, 4-nitrophenyl, 3,5-dinitrophenyl, 4-methoxyphenyl, 2-tolyl, 4-tolyl, The carboxylate salt of this invention has the structural formula:

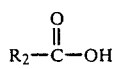

wherein $R_3$ is the same as $R_2$ above and $M^+$ is a monovalent cation such as lithium, sodium, potassium, cesium, silver or tetraalkylammonium.

H-P4-VP-NO is prepared by oxidizing a homopolymer of 4-vinylpyridine using the conditions in Section B described above. The starting material for synthesis of H-P4-VP-NO is commercially available under the trade name Reilline 4200 from Reilly Tar & Chemical Corporation, Indianapolis, Ind.

EXAMPLE VII

All reactions were performed according to the following method unless otherwise noted in Table VII below. Reaction mixtures containing 0.005 mole acid chloride in 15 ml dichloromethane, 0.0055 mole sodium carboxylate and 0.10 equivalent of phase transfer transacylation catalyst H-P4-VP-NO in 15 ml water were stirred vigorously at either ambient temperature (23°–25° C.) or with ice cooling (5° C.) for 5–90 minutes. The organic phase was separated, washed with 10% aqueous potassium carbonate, dried over anhydrous potassium carbonate and rotary evaporated to obtain the product. Table VII below, describes the reactants used in this method, the temperature of reaction, the time period of the reaction, and the anhydrides synthesized.

TABLE VIII

Anhydride Formation in Water - Dichloromethane Mixtures

| Carboxylate Salt | Acid Malide | Catalyst[a] | Temp °C./Time (Min) | Anhydride[b] (%) |
|---|---|---|---|---|
| PhCOO—Na$^+$ | PhCOCl | TEA | rt/30 | 89.1 |
|  |  | PYR | rt/30 | 85.6 |
|  |  | PMO | rt/30 | 87.3 |
|  |  | DMAP | rt/15 | 85.0 |
|  |  | DMAP-NO | rt/5 | 93.2 |
| CH$_3$COO—Na$^+$ | PhCOCl | TEA | rt/30 | 10 |
|  |  | PYR | rt/30 | 50 |
|  |  | PNO | rt/30 | 78 |
| CBZ-Alanine(K$^+$) | PhCOCl | PNO | rt/90 | 96.1 |
| HCOO—Na$^+$ | PhCH=CHCOCl | PNO | rt/30 | 67.7 |
| CH$_3$CH$_2$COO—Na$^+$ | PhCOCl | H—P4-VP-NO | rt/30 | 96.4 |
| (CH$_3$)$_2$CHCOO—Na$^+$ | PhCOCl | H—P4-VP-NO | rt/30 | 95.8 |
| (CH$_3$)$_3$CCOO—Na+ | PhCOCl | H—P4-VP-NO | rt/30 | 85.5 |
|  |  | PNO | rt/30 | 92.5 |
| CH$_2$=CHCOO—HNEt$_3^+$ | PhSO$_2$Cl | DMAP-NO | rt/30 | 53[c] |

[a]TEA is Triethylamine, PYR is Pyridine, PNO is Pyridine, PNO is Pyridine 1-oxide, DMAP is 4-Dimethylamino- pyridine, DMAP—NO is 4-Dimethylamino pyridine 1-oxide LNO is 2,6-Lutidine 1-oxide, H—P4-VP-NO is Poly (4-vinylpyridine 1-oxide).
[b]Product identity and product composition (see notes a and b Table 1)
[c]Anhydride was not isolated, but was converted to N—benzylacrylamide, MP 70-72° C.

A wide variety of mixed anhydrides, including reactive mixed anhydrides of formic and acetic acids and N-blocked amino acids as well as aromatic and aliphatic carboxylic acids are accessible from reactions carried out in mixed aqueous-organic solvent systems. Formation of the mixed anhydride, acrylic benzenesulfonic anhydride demonstrates the application of the method to acids of elements other than carbon. Acylation experiments in which pyridine 1-oxide from 1-acyloxypyridinium ions with phosphoryl haldies as well as benzenesulfonyl chloride and halides of carboxylic acids indicate that the catalysts described herein are capable of accelerating reactions of carbon, sulfur and phosphorus acids. The results summarized in Table VII further demonstrate that a wide variety of tertiary amines and tertiary amine oxides can serve as effective catalysts in formation of most anhydrides. Only the very reactive mixed anhydrides of acetic, alkylcarbonic, and formic acids require the high selectivity of pyridine 1-oxide and polymeric materials that carry pyridine 1-oxide as a pendant group for their preparation.

While the foregoing has been described with respect to preferred embodiments and alternatives thereto, they are not intended nor should they be construed as limitations on the invention. As one skilled in the art would understand many variations and modifications of these embodiments may be made which fall within the spirit and scope of this invention.

We claim:

1. A process for preparing acid anhydrides comprising the step of:
   reacting a carboxylic acid or carboxylate salt with an acid halide or acyl activating agent in the presence of a catalyst selected from the group consisting of a solid phase copolymer of 4-vinylpyridine, a solid phase copolymer of 4-vinylpyridine 1-oxide, and a water soluble homopolymer of 4-vinylpyridine 1-oxide at a temperature of about 0° C. to ambient.

2. A process for preparing acid anhydrides comprising the step of:
   reacting an acid halide with a carboxylic acid or a carboxylate salt in the presence of a catalyst selected from a group consisting of a solid phase copolymer of 4-vinylpyridine and a solid phase copolymer of 4-vinylpyridine 1-oxide at a temperature of about 0° C. to ambient.

3. A process for preparing acid anhydrides comprising the step of:
   reacting an acid halide with a carboxylic acid or a homopolymer of 4-vinylpyridine 1-oxide as a catalyst at a temperature of about 0° C. to ambient.

4. A process for preparing symmetrical acid anhydrides comprising the step of:
   reacting a carboxylic acid or a carboxylate salt with an acyl activating agent in the presence of a solid phase copolymer of 4-vinylpyridine as a catalyst at a temperature of about 0° C. to ambient.

5. A process for preparing acid anhydrides comprising the steps of:
   (a) preparing a column of catalyst selected from a group consisting of a solid phase copolymer of 4-vinylpyridine and a solid phase copolymer of 4-vinylpyridine 1-oxide;
   (b) passing a solution of acid halide and carboxylic acid through the column;
   (c) washing the column with an organic solvent to recover the product.

6. A process for preparing acid anhydrides comprising the steps of:
   (a) preparing a column of catalyst selected from a group consisting of a solid phase copolymer of 4-vinylpyridine and a solid phase copolymer of 4-vinylpyridine 1-oxide;
   (b) passing a solution of acid halide through the column;
   (c) then passing a solution of a carboxylate salt through the column;
   (d) washing the column with an organic solvent to recover the product.

7. A process for preparing acid anhydrides comprising the steps of:

(a) preparing a column of a solid phase co-polymer of 4-vinylpyridine;
(b) passing a solution of carboxylic acid and acyl activating agent through the column;
(c) washing the column with an organic solvent to recover the product;

8. A process for preparing mixed formic anhydride comprising the steps of:
   reacting acid halide with sodium formate in the presence of a solid-phase catalyst selected from the group consisting of a solid-phase co-polymer of 4-vinylpyridine and a solid phase copolymer of 4-vinylpyridine 1-oxide at a temperature of about 0° C. to ambient.

9. The process of claim 1, claim 2, claim 3, claim 5, claim 6 and claim 8 having an acid halide of the structural formula:

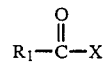

wherein $R_1$ is selected from a group consisting of a saturated or unsaturated alkyl or aralkyl, a substituted or unsubstituted aryl or alkaryl and a alkoxy or aralkoxy and, wherein X is selected from a group consisting of fluorine, chlorine and bromine.

10. The process of claim 1, claim 2, claim 3, claim 5, claim 6 and claim 8 having an acid halide of the structural formula:

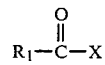

wherein $R_1$ is selected from a group consisting of hydrogen, methyl, ethyl, isopropyl, tert-butyl, n-penyl, n-undecyl, vinyl, isopropenyl, benzyl, styryl, phenyl, biphenylyl, 4-chlorophenyl, 4-nitrophenyl, 3,5-dinitrophenyl, 4-methoxyphenyl, 2-tolyl, 4-tolyl, p-(n-hexyl)phenyl, ethoxy, isobutoxy, and benzyloxy; and wherein X is selected from a group consisting of fluorine, chlorine, and bromine.

11. The process of claim 1, claim 2, claim 3, claim 4, claim 5, and claim 7 having a carboxylic acid of the formula:

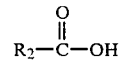

wherein $R_1$ is selected from a group consisting of a saturated or unsaturated alkyl or aralkyl and a substituted or unsubstituted aryl or alkyl.

12. The process of claim 1, claim 2, claim 3, claim 4, claim 5, and claim 7 having a carboxylic acid of the formula:

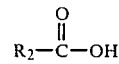

wherein $R_2$ is selected from a group consisting of hydrogen, methyl, ethyl, isopropyl, tert-butyl, n-pentyl, n-undecyl, vinyl, isopropenyl, benzyl, styryl, phenyl, biphenylyl, 4-chlorophenyl, 4-nitrophenyl, 3,5-dinitrophenyl, 4-methoxyphenyl, 2-tolyl, 4-tolyl, and p-(n-hexyl)phenyl.

13. The process of claim 1, claim 2, claim 3, claim 4, and claim 6 having a carboxylate salt of the structural formula:

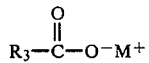

wherein R$_3$ is selected from a group consisting of a saturated or unsaturated alkyl or aralkyl and a substituted and unsubstituted aryl or alkaryl; and wherein M$^+$ is a nonvalent cation.

14. The process of claim 1, claim 2, claim 3, claim 4 and claim 6 having a carboxylate salt of the structural formula:

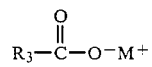

wherein R$_3$ is selected from a group consisting of hydrogen, methyl, ethyl, isopropyl, tert-butyl, n-pentyl, n-undecyl, vinyl, isoprophenyl, benzyl, styryl, phenyl, biphenyl 4-chlorophenyl, 4-nitrophenyl, 3,5-dinitrophenyl, 4-methoxyphenyl, 2-tolyl, 4-tolyl, and p-(n-hexyl)-phenyl; and wherein M$^+$ is a monovalent cation selected from a group consisting of lithium, sodium, potassium, cesium and tetraalkylammonium.

15. The process of claim 1, claim 4 and claim 7 wherein the acyl activating agent is selected from a group consisting of thionyl chloride, phosgene, phosphorus halides and sulfur chlorides.

* * * * *

UNITED STATES PATENT AND TRADEMARK OFFICE
CERTIFICATE OF CORRECTION

PATENT NO. : 4,874,558

DATED : October 17, 1989

INVENTOR(S) : Wilmer K. Fife and Zhi-Dong Zhang

It is certified that error appears in the above-identified patent and that said Letters Patent is hereby corrected as shown below:

Column 1, line 49-50, delete "See R. K. Smalley and H. Suschitzky, J. Chem. Soc. 755 (1964).";

Column 2, line 16-17, delete one instance of "a process for preparing";

Column 6, line 18, delete one instance of "and";

Column 8, line 50 "pyridine N-oxide" should read -- pyridine-N-oxide --;

Table IV, Col. 1, line 24, the formula "P-n-$C_6N_{13}$PhCOCl" should read -- P-n-$C_6H_{13}$PhCOCl --;

Table IV, Col. 1, line 30, the formula "BuOCOCl" should read -- isoBuOCOCl --;

Table IV, Col. 5, line 32-35 should appear as lines 28-31 in Col. 6;

Column 9, line 49, "moities" should be -- moieties --;

Column 13, lines 65-66, after "4-tolyl" add -- and p(n-hexyl)phenyl --; and

Claim 3, lines 37-38, add after "or a" -- carboxylate salt in the presence of a water soluble --.

Signed and Sealed this

Third Day of December, 1991

Attest:

HARRY F. MANBECK, JR.

*Attesting Officer*    *Commissioner of Patents and Trademarks*

UNITED STATES PATENT AND TRADEMARK OFFICE
CERTIFICATE OF CORRECTION

PATENT NO. : 4,874,558

DATED : October 17, 1989

INVENTOR(S) : Wilmer K. Fife and Zhi-Dong Zhang

It is certified that error appears in the above-identified patent and that said Letters Patent is hereby corrected as shown below:

Column 1, line 49-50, delete "See R. K. Smalley and H. Suschitzky, J. Chem. Soc. 755 (1964).";

Column 2, line 16-17, delete one instance of "a process for preparing";

Column 6, line 18, delete one instance of "and";

Table IV, Col. 1, line 30, the formula "BuOCOCl" should read -- isoBuOCOCl --;

Table IV, Col. 5, line 32-35 should appear as lines 28-31 in Col. 6;

Column 9, line 49, "moities" should be -- moieties --;

Column 13, lines 65-66, after "4-tolyl" add -- and p(n-hexyl)phenyl --; and

UNITED STATES PATENT AND TRADEMARK OFFICE
CERTIFICATE OF CORRECTION

PATENT NO. : 4,874,558

DATED : October 17, 1989

INVENTOR(S) : Wilmer K. Fife and Zhi-Dong Zhang

It is certified that error appears in the above-identified patent and that said Letters Patent is hereby corrected as shown below:

Claim 3, lines 37-38, add after "or a" -- carboxylate salt in the presence of a water soluble --.

This certificate supersedes Certificate of Correction issued December 3, 1991.

Signed and Sealed this

Third Day of March, 1992

*Attest:*

HARRY F. MANBECK, JR.

*Attesting Officer*  *Commissioner of Patents and Trademarks*